United States Patent [19]

Azam et al.

[11] 4,134,017

[45] Jan. 9, 1979

[54] RADIATION DEVICE USING A BEAM OF CHARGED PARTICLES

[75] Inventors: Guy Azam; Claude Perraudin, both of Buc France, France

[73] Assignee: C.G.R.-MeV, Buc France, France

[21] Appl. No.: 812,734

[22] Filed: Jul. 5, 1977

[30] Foreign Application Priority Data

Jul. 9, 1976 [FR] France .................................. 76 21106

[51] Int. Cl.² ............................................. H01J 29/00
[52] U.S. Cl. ................................. 250/398; 250/396 R
[58] Field of Search ............. 250/396 R, 396 ML, 37, 250/398, 296, 297, 298, 299, , 385; 313/361, 433

[56] References Cited

U.S. PATENT DOCUMENTS 3,405,363  10/1968  Brown .................................. 250/396
3,691,374  9/1972  Lebout et al. ......................... 250/396
3,997,788  12/1976  Boux .................................... 250/385

Primary Examiner—Bruce C. Anderson
Attorney, Agent, or Firm—Karl F. Ross

[57] ABSTRACT

A beam of charged particles is guided along a path including a looped section between two rectilinear stretches, each of these stretches being provided with focusing and centering means. A holder insertable into the outgoing stretch, ahead of a collimator, carries a target designed to emit photons upon being struck by incident particles. The target holder is linked with a retracting mechanism which also controls a diaphragm in the looped path section to narrow its aperture when the target is in place. A dose-equalizing filter utilized in the latter instance is movable jointly with the target holder out of the path of the exiting beam.

10 Claims, 6 Drawing Figures

RADIATION DEVICE USING A BEAM OF CHARGED PARTICLES

FIELD AND BACKGROUND OF THE INVENTION

Radiation beams in general and, more particularly, those used in radiotherapy applications must possess certain characteristics the most important of which are:
  well-defined dimensions and energy;
  proper centering in relation to the target or the zone to be treated;
  uniformity;
  suitable directivity.

Moreover, if the radiation beam is composed of accelerated electrons, this beam must not be contaminated by parasitic photons which would otherwise modify the distribution of the radiation dose intended to have a predetermined value for a given treatment.

OBJECT OF THE INVENTION

An object of our present invention is to provide a device capable of producing a beam of charged particles which satisfies the aforestated desiderata and is free from accompanying photons.

Another object is to provide a device of this type which can be utilized for the selective generation of electron and photon beams.

SUMMARY OF THE INVENTION

In accordance with our present invention, we provide a source of accelerated charged particles — such as electrons — which are formed into a beam by focusing means disposed downstream of that source. A predetermined beam path, designed to eliminate photons accompanying the charged particles, is defined by guide means including first magnetic centering means establishing a rectilinear entrance stretch, second magnetic centering means establishing a rectilinear exit stretch, and a stigmatic and a chromatic magnetic deflector establishing a curved path section between these two stretches. The guide means may also include a collimator at the end of the exit stretch. A diaphragm of adjustable aperture is disposed in the curved path section for varying the intensity of the exiting beam. This curved section may be a loop extending over an arc of about 270° resulting in a substantially orthogonal intersection of the rectilinear stretches which merge tangentially into the loop. Advantageously, pursuant to a more particular feature of our invention, the diaphragm is coupled with a retraction mechanism which is linked with a movable holder for a photon-emissive target interposable in the beam path on the exit stretch. When the target is operatively positioned for excitation by impinging electrons to emit a photonic beam, the diaphragm aperture is narrowed whereby the beam is reduced in intensity and is more sharply focused upon the target.

BRIEF DESCRIPTION OF THE DRAWING

The above and other features of our invention will now be described in detail with reference to the accompanying drawing in which.

SPECIFIC DESCRIPTION

Figure 1:
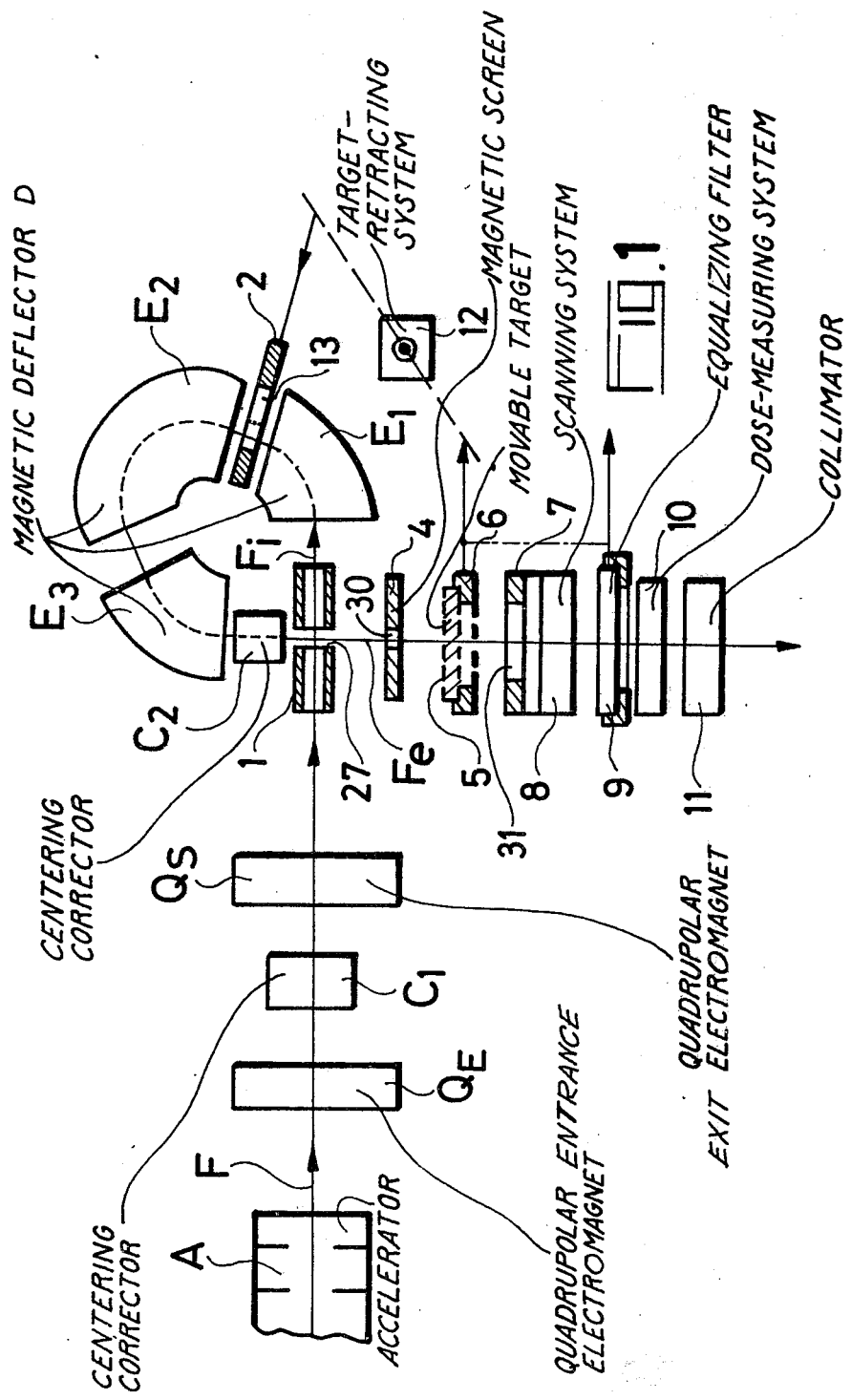
FIG. 1 schematically illustrates a radiation device embodying our invention.

A radiation device in accordance with the invention, shown schematically in FIG. 1, comprises:

a linear accelerator A of charged particles (electrons in the example illustrated) producing a beam F:

a magnetic focusing doublet constituted by a quadrupolar entrance electromagnet $Q_E$ and a quadrupolar exit electromagnet $Q_S$;

a first centering corrector $C_1$ arranged between the entry and exit quadrupolar electromagnet $Q_E$ and $Q_S$, in the path of the beam F;

a tubular magnetic shield 1 arranged along the path of the beam downstream of the exit quadrupolar electromagnet $Q_S$, the axis of shield 1 corresponding to the mean path of the beam;

a magnetic deflector D consisting of three sectoral electromagnets $E_1$, $E_2$, $E_3$ making it possible to deflect the incident beam $F_i$ through an angle $\phi$ equal to 270°, this magnetic deflector D being of the stigmatic and achromatic type disclosed in U.S. Pat. No. 3,691,374;

a diaphragm 2 having an aperture in the form of a slot 13 of adjustable width, arranged between the electromagnets $E_1$ and $E_2$ at the energy focus of the first electromagnet $E_1$;

a second centering corrector $C_2$ arranged at the exit of the electromagnet $E_3$ of the magnetic deflector;

a magnetic screen plate 4 of mild steel, arranged perpendicularly to the mean path of the beam $F_e$ emerging from the magnetic deflector D, the plate 4 being provided with an opening 30 to pass the beam $F_e$;

a scanning system 8 comprising a quadrupolar electromagnet;

a shield plate 7 integral with the scanning system 8 and arranged upstream of the latter, this plate having a fixed diaphragm aperture 31;

a dose-measuring system 10 which makes it possible to check the radiation doses produced by the beam $F_e$ as well as to check the centering, uniformity and directivity of this beam (a dose-measuring system of this kind has been described in commonly owned U.S. patent application Ser. No. 835,361); and a collimator 11 of the kind described, for example, in commonly owned U.S. patent application Ser. No. 500,742.

Figure 2:
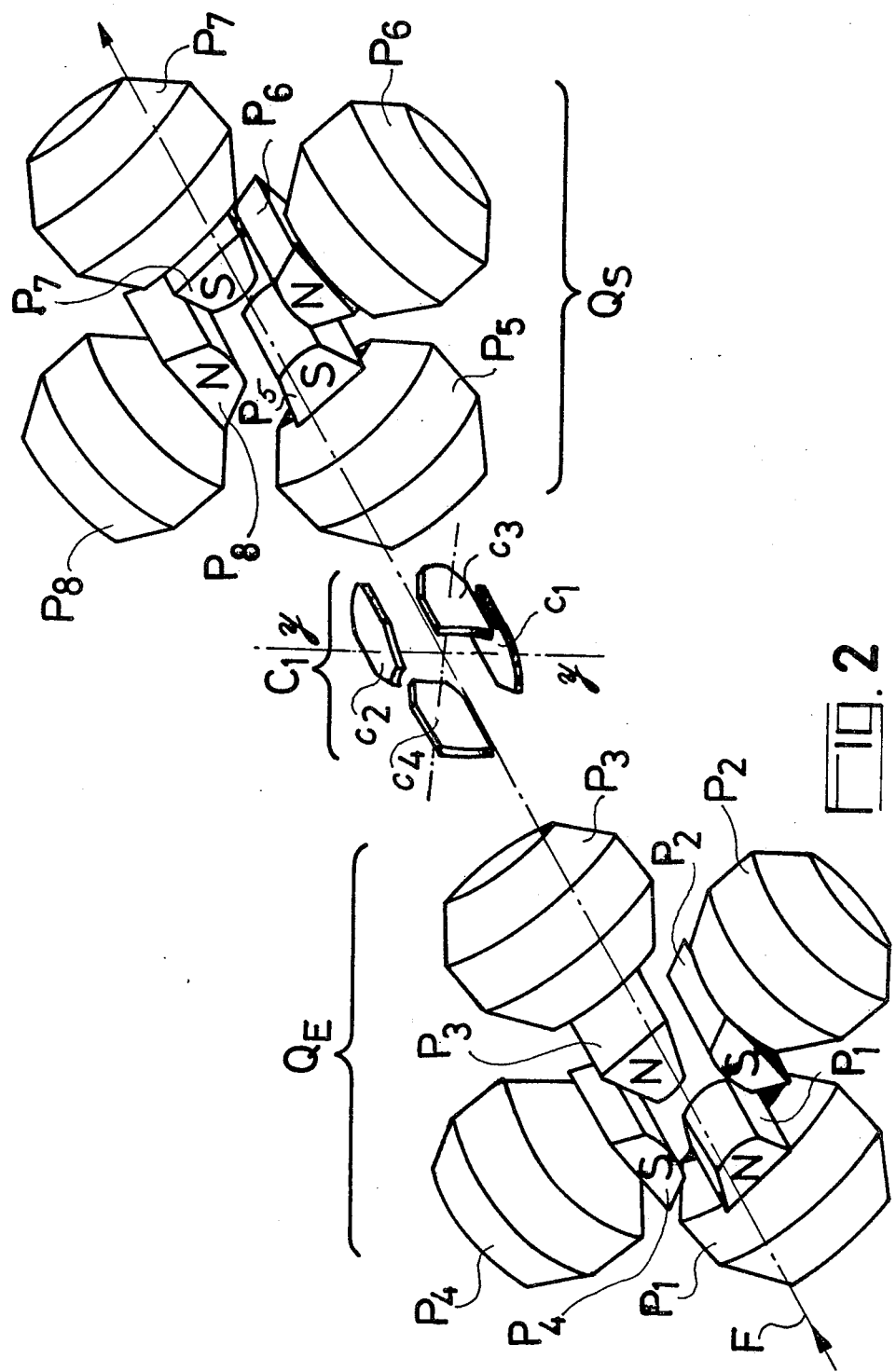
FIG. 2 illustrates a magnetic doublet, serving to focus a charged-particle beam in two orthogonal planes, and an associated centering corrector.

The quadrupolar electromagnets $Q_E$ and $Q_S$ of the magnetic focusing doublet are more fully illustrated in FIG. 2. The entrance electromagnet $Q_E$ comprises two electromagnetic members (not shown) respectively associated with four pole pieces $P_1$, $P_2$, $P_3$, $P_4$ which are solids of revolution and are equipped with supplemental elements or pole shoes $p_1$, $p_2$, $p_3$, $p_4$ of generally trapezoidal profile. The exit electromagnets $Q_S$ also comprises four pole pieces $P_5$, $P_6$, $P_7$, $P_8$ which are solids of revolution and are equipped with supplemental pole shoes $p_5$, $p_6$, $p_7$, $p_8$.

Figures 3, 4:
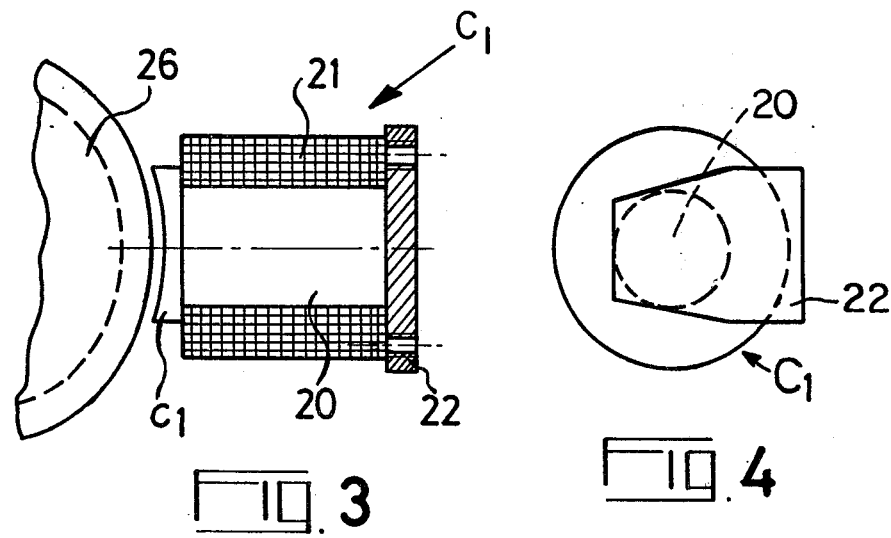
FIGS. 3 and 4 respectively represent elevational and face views of a detail of the centering corrector.

The first centering corrector $C_1$ is of small size. It facilitates the correction of defects in the centering of the beam F in two directions defined by mutually orthogonal axes xx and yy. This centering corrector $C_1$ comprises two pairs of electromagnets respectively equipped with pole pieces $c_1$, $c_2$, $c_3$, $c_4$ (see FIG. 2) matching the shapes of a sealed tubular passage 26 (FIG. 3) through which the beam passes. FIGS. 3 and 4 illustrate (in elevation and in face view) a detail of the electromagnet used in the centering corrector $C_1$ and included in the radiation device in accordance with the invention. The pole piece $c_1$ is carried by a core 20 associated with a coil 21. The core 20 is integral with a yoke 22 which can be attached to the wall of the radiation device. The position of one of the pairs of pole pieces ($c_1$, $c_2$ for example) is adjustable in relation to the others ($c_3$, $c_4$). Moreover, the adjustable voltages applied to each pair of coils makes it possible to achieve a fine correction of the centering of the beam F. By way of example, the corrector $C_1$ as described and illustrated here, when designed for an electron beam having an energy of 20 Mev, is contained within a cube of 30 mm side length.

The radiation device in accordance with the invention as described above produces a radiation beam constituted by accelerated electrons. The device is also designed to be able to supply a beam of photons. A movable target 5 (FIG. 1) can be disposed for this purpose downstream of the magnetic screen plate 4. The target 5 is carried by a holder 6 associated with a retracting system 12 which enables withdrawal of the target 5 when the radiation device is to produce an electronic instead of a photomic radiation beam. The translatory motion (in a plane perpendicular to the beam) of this target 5 is accompanied by a variation in the width of the slot 13 in the diaphragm 2. One part of this diaphragm (i.e. the one located at the left of the slot 13 in FIG. 1) is fixed whereas the other part is movable and is coupled to the retracting system 12. The slot 13 has its maximum width when the target 5 is located in the trajectory of the emergent beam $F_e$, narrowing automatically when the target 5 is displaced out of the path. A movable dose-equalizing filter 9 is associated with the target 5 and lies in the path of the radiation beam when the target 5 itself is disposed in that path, as indicated diagrammatically in FIG. 1.

Figures 5, 6:
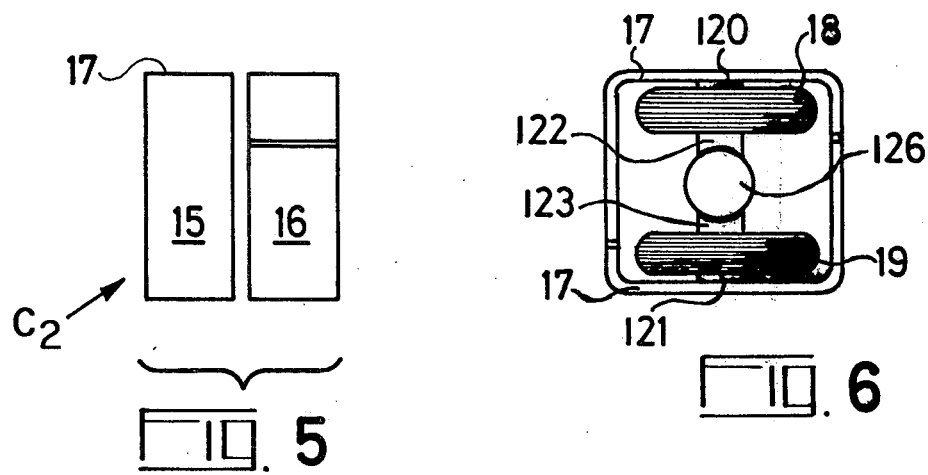
FIGS. 5 and 6 illustrate, in elevation and in face view, a second centering corrector.

It should be pointed out that the tubular magnetic shield 1 extending along the path of the incident beam $F_i$ upstream of the electromagnet $E_1$ protects this beam $F_i$ against the parasitic magnetic effects produced by the second corrector $C_2$ centering the emergent beam $F_e$. An example of this second centering corrector $C_2$ has been shown in FIG. 5. It comprises two pairs of electromagnets 15 and 16 arranged one behind the other and designed to center the emergent beam in two mutually orthogonal planes. Each pair of electromagnets is surrounded by a magnetic shield 17, formed by two mild-steel half-shells, and comprises coils 18, 19 provided with cores /20,/21 terminating in pole-pieces/22, /23 matching the shape of a sealed tubular passage /26 traversed by the electron beam $F_e$ passing through a gap 27 of the magnetic shield 1 in line with opening 30 (FIG. 1). The incident and emergent beams $F_i$ and $F_e$ are protected against the parasitic effects of the magnetic fields, used during the operation of the radiation device, by the presence of the shields 1 and 17 associated with the corrector $C_2$ and by the screen plate 4.

The radiation device in accordance with the invention makes it possible to produce a suitably centered, uniform radiation beam having well-defined dimensions and a predetermined dose level. The diaphragm 2 of adjustable aperture enables the generation of an electron beam of preselected intensity. Moreover, the signals picked off at the edges of the slot 13 can be employed for accurate control of the energy of the radiation beam.

It should be pointed out, also, that the known radiation devices generally used diffuser sheets in order to produce an electron beam of given dimensions, but these have the drawback of emitting parasitic photons which may modify the characteristics of the radiation beam. The quadrupolar beam-guiding system used in the device in accordance with the invention makes it possible to obtain an electron beam containing no photons at all, thanks to the deflection of the charged particles along a loop by the electromagnets $E_1 - E_3$. Moreover, a large treatment zone can be swept by the beam on account of the scanning system 8 which may be of the kind described in commonly owned U.S. patent application Ser. No. 768,907.

The device 10 measuring the dose level could be inserted between a pre-collimator (not shown) and the collimator 11. This measuring device monitors the intensity, uniformity, centering and directivity of the radiation beam in the neighborhood of the zone to be treated. Measuring device of this kind have been described in commonly owned U.S. Pat. No. 3,997,788.

We claim:
1. A radiation device comprising:
    a source of accelerated charged particles;
    focusing means downstream of said source for forming said charged particles into a beam;
    guide means defining a predetermined path for said beam, said guide means including first magnetic centering means establishing a rectilinear entrance stretch, second magnetic centering means establishing a rectilinear exit stretch, and a stigmatic and achromatic magnetic deflector establishing a curved path section between said entrance and exit stretches; and
    a diaphragm of adjustable aperture in said curved path section for varying the intensity of the exiting beam.

2. A radiation device as defined in claim 1 wherein said magnetic deflector comprises a plurality of sectoral electromagnets, said diaphragm being located at an energy focus of one of said electromagnets.

3. A radiation device as defined in claim 2 wherein said electromagnets define a loop extending over an arc of substantially 270°, said entrance and exit stretches being substantially perpendicular to each other and merging tangentially into said loop.

4. A radiation device as defined in claim 3, further comprising magnetic shield means disposed near the intersection of said stretches, said second centering means being disposed between said loop and said intersection.

5. A radiation device as defined in claim 4 wherein said magnetic shield means comprises a pair of coaxial tubes centered on one of said stretches and separated by a gap, said intersection lying in said gap.

6. A radiation device as defined in claim 5 wherein said tubes are centered on said entrance stretch and said gap is traversed by said exit stretch, said shield means further comprising a plate having an opening in line with said gap.

7. A radiation device as defined in claim 4, further comprising scanning means along said exit stretch downstream of said shield means.

8. A radiation device as defined in claim 1, further comprising a movable holder for a photon-emissive target interposable in the beam path on said exit stretch, and retracting means linked with said holder for withdrawing said target from said beam path, said diaphragm being coupled with said retracting means for narrowing said aperture upon the interposition of said target in the beam path.

9. A radiation device as defined in claim 8, further comprising a movable dose-equalizing filter interposable in said exit stretch downstream of said holder and coupled therewith for joint withdrawal.

10. A radiation device as defined in claim 1 wherein said focusing means includes a pair of quadrupolar electromagnets bracketing said first centering means, said guide means further comprising a collimator downstream of said second centering means.

* * * * *